United States Patent [19]

Fujiwara

[11] Patent Number: 4,895,975

[45] Date of Patent: Jan. 23, 1990

[54] DIACETYLENE COMPOUND AND PROCESS FOR PRODUCTION OF POLYMER CONTAINING DIACETYLENE GROUPS FROM THE DIACETYLENE COMPOUND

[75] Inventor: Eisuke Fujiwara, Ami, Japan

[73] Assignee: Kozo Iizuka, Director-General of Agency of Industrial Science and Technology, Tokyo, Japan

[21] Appl. No.: 165,906

[22] Filed: Mar. 9, 1988

[30] Foreign Application Priority Data

May 6, 1987 [JP] Japan .................................. 62-108974

[51] Int. Cl.$^4$ ............................................ C07C 63/24
[52] U.S. Cl. ..................... 560/083; 528/125; 528/128; 528/171; 528/172; 528/173; 528/176; 528/183; 528/191; 528/192; 528/345; 528/348; 560/76; 562/488; 562/850; 562/853
[58] Field of Search ................... 562/488; 560/83, 76; 260/544 D; 523/202; 525/328

[56] References Cited

U.S. PATENT DOCUMENTS 4,657,708  4/1987  Evers et al. .................... 260/544 D

OTHER PUBLICATIONS

Chemical Abstracts; vol. 106, 1987, 176,091(b), pp. 700-701 (Acheson).

*Primary Examiner*—Harold D. Anderson
*Assistant Examiner*—T. Mosley
*Attorney, Agent, or Firm*—Oblon, Spivak, McClelland, Maier & Neustadt

[57] ABSTRACT

A diacetylene compound of the formula:

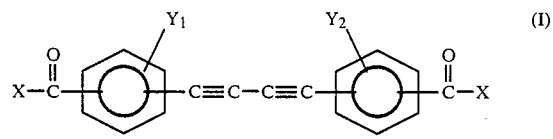

wherein X is a hydroxyl group, a halogen atom, an alkoxy group, a monovalent hydrocarbon group having from 1 to 20 carbon atoms or a —OM group wherein M is an alkali metal, and each of $Y_1$ and $Y_2$ which may be the same or different is a hydrogen atom, a monovalent organic group having from 1 to 20 carbon atoms or a halogen atom.

Further described a process for producing a polymer containing diacetylene group in its main chain using a diacetylene compound of the above.

9 Claims, 5 Drawing Sheets

DIACETYLENE COMPOUND AND PROCESS FOR PRODUCTION OF POLYMER CONTAINING DIACETYLENE GROUPS FROM THE DIACETYLENE COMPOUND

BACKGROUND OF THE INVENTION

1. Field of the Invention

The present invention relates to a compound containing a diacetylene group in its molecule, which is useful as a starting material for photofunctional materials and highly rigid polymers, and a process for producing a polymer containing readily cross-likable diacetylene groups in its main polymer chain from such a compound.

The diacetylene compound can readily be converted to a polydiacetylene by topochemical polymerization of the diacetylene group and thus is useful as the starting material for various photofunctional materials.

Further, the polymer containing diacetylene groups obtained from the diacetylene compound of the present invention can be molded by a conventional method for molding polymers, and then the diacetylene groups can be cross-linked to obtain a densely cross-linked highly rigid shaped product having excellent thermal properties. Further, it can be molded together with an inorganic or organic filler, a pigment, an ultraviolet absorber, a stabilizer or the like, and the product is useful as a structural material.

Further, the product thereby obtained is cross-liked by πelectron conjugations, and, when doped, is useful as an electrically conductive material or a highly functional material such as a nonlinear optical material

2. Discussion of Background

As a compound containing a diacetylene group in its molecule, a number of compounds have been known wherein the neighboring-group of the diacetylene group is an aliphatic group. Further, with respect to a compound wherein the neighboring-group is an aromatic group, some compounds have been known wherein the aromatic ring is unsubstituted or substituted by an amino group, a nitro group or the like. (Gerhard Wegner, (Polymer Letters), 9, p.133–144 (1971); Barbara Grant, (Mol. Cryst. Liq. Cryst.), 48, p.175–182 (1978)).

It is well known that among these diacetylene compounds, certain diacetylene compounds undergo polymerization of the diacetylene groups in their crystal state by heat or high energy rays such as γ-rays or ultraviolet rays (topochemical polymerization). (G. Wegner, Z. Naturforschg., 246, p.824 (1969); G. Wegner, Makromol. Chem., 134, p.219 (1970); G. Wegner, J. Polym. Sci., 89, p.133 (1971)).

With respect to these diacetylene compounds, many researches have been conducted concerning their topochemical polymerization and application of the topochemical polymer to photofunctional materials or the like.

However, there have so far been only a few research reports on a polymer containing a diacetylene group in the main polymer chain. (Makuromol. Chem., 134, p.219 (1970) and J. Polym. Sci. Polym. Chem. Ed., 19, p.1154 (1981)).

There has been no attempt to develop a polymer capable of isotropically providing a high modulus of elasticity by subjecting a polymer containing diacetylene groups to the three-dimensional cross-linking reaction.

The present inventors conducted extensive researches to make use of the high reactivity of diacetylene groups to obtain the shaped product having isotropically high rigidity and excellent heat resistance, and they found that a highly rigid shaped product could be obtained by molding a polyester or polyurethane containing diacetylene groups in its solid phase at a temperature below the decomposition temperature or melting point thereof under a high pressure condition. (U.S. Pat. No. 4,654,178).

However, the polymer containing diacetylene groups produced from the diacetylene compound having an aliphatic group as the neighboring-group of the diacetylene group, has the limitation in its heat resistance, and no shaped product having fully satisfactory properties has been obtained yet. Therefore, it is desired to develop a material capable of providing a shaped product having higher rigidity and improved heat resistance.

SUMMARY OF THE INVENTION

With respect to compounds having an aromatic group as the neighboring-group of the diacetylene group, no compound having an aromatic ring substituted by a carbonyl group has been known.

The present inventors have conducted extensive researches on the process for producing a novel diacetylene compound, and have found a novel diacetylene compound having a carbonyl group introduced to an aromatic ring being a neighboring-group of the diacetylene group. The present invention has been accomplished on the basis of this discovery.

The present invention provides a diacetylene compound of the formula:

wherein X is a hydroxyl group, a halogen atom, an alkoxy group, a monovalent hydrocarbon group having from 1 to 20 carbon atoms or a —OM group wherein M is an alkali metal, and each of $Y_1$ and $Y_2$ which may be the same or different is a hydrogen atom, a monovalent organic group having from 1 to 20 carbon atoms or a halogen atom.

The present invention further provides a process for producing a polymer containing diacetylene groups in its main polymer chain, which comprises condensation polymerization of a diacetylene compound of the formula I with a diamino compound or/and a dihydroxyl compound.

DETAILED DESCRIPTION OF THE PREFERRED EMBODIMENTS

The diacetylene compound of the present invention is a compound having aromatic rings substituted by carbonyl groups, as neighboring-groups of the diacetylene group as shown by the above formula I.

According to the present invention, the halogen atom for X in the formula I, is preferably Cl, Br or I. Cl or Br is usually used.

The alkoxy group for X in the formula I may, for example, be $CH_3-O-$, $C_2H_5-O-$, $C_3H_7-O-$, $C_4H_9-O-$, $C_5H_{11}-O-$, $C_6H_{13}-O-$, wherein $R_1$ is a substituent of an aromatic ring, and it is a hydrogen atom, a halogen atom, an alkyl group or a nitro group. An alkoxy group having from 1 to 6 carbon atoms is usually used.

The monovalent hydrocarbon having from 1 to 20 carbon atoms for X in the formula I, may, for example, be $CH_3-$, $C_2H_5-$, $C_3H_7-$, $C_4H_9-$, $C_5H_{11}-$, $C_6H_{13}-$, $C_2H_5-$, $C_3H_7-$, $C_4H_9-$, $C_5H_{11}-$, $C_6H_{13}-$, wherein $R_2$ is as defined above with respect to $R_1$ in the case of the alkoxy group.

As the alkali metal for M in the —OM group for X in the formula I, Li, Na, K or Rb may be mentioned and Na or K is usually used. Further, an alkaline earth metal may employed in place of the alkali metal. As such an alkaline earth metal, Be, Mg, Ca, Sr or Ba may be mentioned.

$Y_1$ and $Y_2$ in the formula I may be the same or different, and each represents a hydrogen atom or a halogen atom or a monovalent organic group having from 1 to 12 carbon atoms. As the halogen atom, F, Cl, Br or I may be mentioned. As the monovalent organic group having from 1 to 12 carbon atoms, $C_3H_7-$, $C_4H_9-$, $C_5H_{11}-$, $C_6H_{13}-$, may be mentioned. A part or all of hydrogen atoms of these organic groups may be substituted by a functional group such as a halogen atom, a nitro group, an amino group, a cyano group, a carbonyl group, a carboxyl group, an alkoxyl group or an amide group.

Further, the hydrogen atom may be substituted with a monovalent hydrocarbon group having from 1 to 20 carbon atoms, by an ether linkage, an ester linkage, an amide linkage or an amino linkage. As specific examples of the diacetylene compound of the formula I, there may be mentioned ester type butadiynes such as
1,4-bis(4-methoxycarbonylphenyl)-butadiyne,
1,4-bis(4-ethoxycarbonylphenyl)-butadiyne,
1,4-bis(4-butoxycarbonylphenyl)-butadiyne,
1,4-bis(4-phenoxycarbonylphenyl)-butadiyne,
1,4-bis(4-benzyloxyphenyl)-butadiyne,
1,4-bis(3-methoxycarbonylphenyl)-butadiyne,
1,4-bis(3-ethoxycarbonylphenyl)-butadiyne,
1,4-bis(3-phenoxycarbonylphenyl)-butadiyne,
1,4-bis(3-methyl-4-methoxycarbonylphenyl)-butadiyne,
1,4-bis(3-methyl-4-ethoxycarbonylphenyl)-butadiyne,
1,4-bis(3-chloro-4-methoxycarbonylphenyl)-butadiyne,
1,4-bis(3-chloro-4ethoxycarbonylphenyl)-butadiyne and
1,4-bis(2-chloro-4-ethoxycarbonylphenyl)-butadiyne;
ketone type butadiynes such as
1,4-bis(4-methylcarbonylphenyl)-butadiyne,
1,4-bis(4-ethylcarbonylphenyl)-butadiyne,
1,4-bis(4-phenylcarbonylphenyl)-butadiyne,
1,4-bis(3-methylcarbonylphenyl)-butadiyne,
1,4-bis(3-ethylcarbonylphenyl)-butadiyne,
1,4-bis(3-methyl-4-methylcarbonylphenyl)-butadiyne,
1,4-bis(2-methyl-4-methylcarbonylphenyl)-butadiyne,
1,4-bis(3-methyl-5-methylcarbonylphenyl)-butadiyne,
1,4-bis(3-chloro-4-ethylcarbonylphenyl)-butadiyne and
1,4-bis(3-chloro-5-ethylcarbonylphenyl)-butadiyne;
carboxylic acid type butadiynes such as
1,4-bis(4-hydroxycarbonylphenyl)-butadiyne,
1,4-bis(3-hydroxycarbonylphenyl)-butadiyne,
1,4-bis(3-methyl-4-hydroxycarbonylphenyl)-butadiyne,
1,4-bis(3-ethyl-4-hydroxycarbonylphenyl)-butadiyne,
1,4-bis(3-methyl-5-hydroxycarbonylphenyl)-butadiyne,
1,4-bis(2-ethyl-5-hydroxycarbonylphenyl)-butadiyne,
1,4-bis(3-chloro-4-hydroxycarbonylphenyl)-butadiyne,
1,4-bis(3-chloro-5-hydroxycarbonylphenyl)-butadiyne, 1,4-bis(2-chloro-4-hydroxycarbonylphenyl)-butadiyne and
1,4-bis(2-chloro-3-hydroxycarbonylphenyl)-butadiyne;
alkali metal salts of the above carboxylic acid type butadiynes such as
1,4-bis(4-sodiumoxycarbonylphenyl)-butadiyne,
1,4-bis(3-sodiumoxycarbonylphenyl)-butadiyne and
1,4-bis(4-potassiumoxycarbonylphenyl)-butadiyne;
and acid halides of the above carboxylic acid type butadiynes such as
1,4-bis(4-chloroformylphenyl)-butadiyne,
1,4-bis(3-chloroformylphenyl)-butadiyne,
1,4-bis(3-methyl-4-chloroformylphenyl)-butadiyne,
1,4-bis(2-methyl-4-chloroformylphenyl)-butadiyne,
1,4-bis(3-chloro-4-chloroformylphenyl)-butadiyne,
1,4-bis(3-chloro-5-chloroformylphenyl)-butadiyne,
1,4-bis(4-bromoformylphenyl)-butadiyne and
1,4-bis(3-bromoformylphenyl)-butadiyne.

Process for production of the diacetylene compound

The diacetylene compound of the formula I can be produced in accordance with the reaction scheme shown by the following reaction formulas (a)–(f). In the reaction formulas (a)–(f), X, $Y_1$ and $Y_2$ are as defined with respect to the formula I. In order to distinguish the species in X, an alkali metal is represented by M and a halogen atom is represented by Hal. When $Y_1$ and $Y_2$ are the same they are represented by Y.

The reaction formula (a) shows a route for the production of the diacetylene compound by the coupling reaction of an ethynyl compound. The reaction formulas (b) and (c) show the hydrolysis of a diacetylene diester compound for the production of an alkali metal salt and a diacetylene dicarboxylic acid compound. The reaction formula (d) shows a route for the production of a diacetylene dicarboxylic acid dihalide by the reaction for conversion to acid halide of a diacetylene dicarboxylic acid compound, its alkali metal salt or a diacetylene diester compound.

(a)

(1)

(2)

(b)

(2)

(3)

(c)

(3)

(4)

Further, the diacetylene dicarboxylic acid compound can be directly produced by the oxidative coupling reaction of an ethynyl benzoic acid as shown by reaction formula (e).

The compound of the formula 4

The compound of the formula 4 (e)

A compound wherein $Y_1$ and $Y_2$ are different, can be produced according to the reaction formula (f) by the oxidative coupling reaction of different species of ethynyl compounds.

Now, the process for production of the diacetylene compound of the present invention will be described in detail with reference to specific Examples.

(1) Production of a diphenylbutadiyne dicarboxylic acid diaralkyl ester and a diphenylbutadiyne diaralkyl ketone of the formula 2

According to the reaction formula (a), an ethynyl benzoic acid aralkyl ester and an ethynyl benzene aralkyl ketone as starting materials, are subjected to oxidative coupling in the presence of a catalyst to obtain the desired butadiyne compound of the formula 2.

As the catalyst for the oxidative coupling reaction, a copper salt or a cobalt salt may be employed. Further, as a co-catalyst, an amine or an alkaline compound may be used. As the catalyst system, a copper salt/tertiary amine, a copper salt/bidentate tertiary amine, a manganese salt/oxime/alkaline compound or a cobalt salt/oxime/alkaline compound may be employed. Among them, the combination of the copper salt/bidentate tertiary amine is preferred since it provides a high reaction rate.

As the metal salts, there may be employed cuprous chloride, cupric chloride, cuprous bromide, cupric bromide, cuprous sulfate, cupric sulfate, manganese (II) chloride, manganese (II) bromid, manganese (II) iodide, manganese (II) carbonate, manganese (II) acetate, manganese (II) nitrate, cobalt (II) chloride, cobalt (II) bromide, cobalt (II) iodide or the like.

As the tertiary amine used as the co-catalyst, pyridine or triethylamine may be mentioned, and as the bidentate tertiary amine, an N,N,N,N-tetraalkylalkylenediamine, an N,N,N-trialkylalkylenediamine or an N,N-dialkylalkylenediamine may be mentioned, where the alkyl group is preferably a methyl group or an ethyl group. As the oxime, α-benzoinoxime may be mentioned. As the alkaline compound, sodium hydroxide, potassium hydroxide or the like may be employed.

For the oxidative coupling of an alkyl ethynyl benzoate, the reaction may be conducted by using a catalyst in an amount of from 0.1 to 100% to the ethynyl compound. If the amount of the catalyst is too small, the yield of the product tends to be low due to deactivation of the catalyst. On the other hand, it is not practical to use an excessive amount because the cost of the catalyst will be high. The amount of the catalyst is preferably within a range of from 1 to 30% to the ethynyl compound. Further, the co-catalyst shows the highest activity when used in an amount of about 1 mol to 1 mol of the catalyst.

There is no particular restriction as to the solvent to be used for the oxidative coupling reaction so long as it can dissolve the starting material ethynyl compound and it is inert to the catalyst used. At a preferable solvent, an alcohol solvent such as methanol or ethanol, a ketone solvent such as acetone or methyl ethyl ketone, an ether solvent such as tetrahydrofurun or 1,4-dioxane or a chlorine type solvent such as chloroform or dichloromethane, may be employed. There is no particular restriction as to the amount of the solvent used. However, it is used usually in an amount of from twice to ten times to the ethynyl compound.

Oxygen may be used for the reaction as it is or as diluted with an inert gas such as nitrogen. Further, it is possible to use air. The reaction is preferably conducted under oxygen stream.

The reaction temperature is generally up to 100° C. and usually within a range of from 20 to 80° C. In order to prevent undesirable side reactions, it should be avoided to conduct the reaction at a high temperature.

The reaction is terminated by pouring the reaction mixture into a poor solvent for the product thereby to precipitate the reaction product, or by adding an acid or base capable of reacting with the catalyst to destroy the catalyst.

Then, the product is separated by filtration, washed, and dried under reduced pressure to obtain the desired butadiyne compound of the formula 2. It is also possible for certain particular purposes to further purify the butadiyne compound of the formula 2 by recrystallization, sublimantion or the like.

Further, a compound of the present invention having different $Y_1$ and $Y_2$ as the substituents of the aromatic rings, can be produced by Cadiot-Chodkiewicz coupling reaction shown by the reaction formula (f). In this reaction, the hydrogen atom of one ethynyl group is substituted by a halogen atom, followed by the coupling with the other ethynyl group. Namely, a halogenated ethynyl compound is produced by the reaction of an ethynyl compound with sodium hypochlorite, sodium hypoiodite, sodium hypobromite, sodium hypofluorite or the like, and subsequently the halogenated ethynyl compound and an ethynyl compound are subjected to the coupling reaction by using a metal catalyst such as copper acetate, cuprous chloride, cupric chloride, cuprous bromide, cupuric bromide, cuprous sulfate or cupric sulfate, to obtain the desired butadiyne compound of the formula 2.

(2) Production of a diphenylbutadiynedicarboxylic acid dialkali metal salt of the formula 3 and a diphenylbutadiynedicarboxylic acid of the formula 4

According to the reaction formula (b), the above diphenylbutadiynedicarboxylic acid diaralkyl ester is hydrolyzed in the presence of a base or an acid to obtain the desired diphenylbutadiynedicarboxylic acid dialkali metal salt of the formula 3.

As the catalyst for the hydrolysis, an alkali metal hydroxide such as sodium hydroxide, potassium hydroxide or lithium hydroxide, or a mineral acid such as hydrochloric acid or sulfuric acid, is generally used. Preferred is sodium hydroxide, potassium hydroxide or the like. Water is usually used as a solvent for the hydrolysis, and the hydrolysis may be conducted in a solvent mixture of water and other solvent miscible with water. The diphenylbutadiynedicarboxylic acid dialkali metal salt of the formula 3 may be isolated from the reaction solution and purified. However, it may be used without isolation or purification for the subsequent production of the dicarboxylic acid shown by the reaction formula (c). Namely, a mineral acid such as hydrochloric acid, sulfuric acid or nitric acid is added to the reaction solution of the hydrolysis to precipitate the dicarboxylic acid of the formula 4, and then the product is separated by filtration, washed and dried under reduced pressure to obtain the diphenylbutadiynedicarboxylic acid of the formula 4. There is no particular restriction as to the concentration of sodium hydroxide or the like used for the hydrolysis. There is also no particular restriction as to the reaction temperature and the reaction time. The reaction temperature is preferably from 20 to 120° C., and the reaction time is preferably from 20 minutes to 10 hours. It is possible for certain particular purposes to further purify the product by recrystallization, sublimantion or the like.

(3) Production of the diphenylbutadiynedicarboxylic acid halide of the formula 5

The diphenylbutadiynedicarboxylic acid halide of the formula 5 can be produced by reacting a corresponding dicarboxylic acid, dicarboxylic acid dialkali metal salt or dicarboxylic acid diester, with an inorganic halide or an organic halide, as shown by the reaction formula (d).

As the inorganic halide, phosphoryl chloride, thionyl chloride, phosphorus pentachloride, phosphorus trichloride, phosphorus tribromide or triphenylhalophosphonium chloride may be used. Further, zinc chloride, pyridine, iodine, triethylamine, dimethylformamide or hexamethylphosphor amide may be employed as a catalyst in an addition to the above inorganic halide. As the organic halide, benzoyl chloride, an oxalylic chloride, phthalic dichloride, benzoyl fluoride, or triphenyl phosphine and carbon tetrachloride may be used. Thionyl chloride or phophorus tetrachloride is preferably used because of its economical advantage.

The reaction is conducted by heating in a large excess amount of a halogenating agent. The reaction time is from 2 to 24 hours. After completion of the reaction, the halogenating agent is removed to obtain the desired diphenylbutadiynedicarboxylic acid halide of the formula 5. It is possible for certain particular purposes to further purify the product by recrystallization, sublimantion or the like.

The process for producing a polymer containing diacetylene groups in its main polymer chain according to the present invention is characterized in that a diacetylene compound of the formula I having certain specific X i.e. a diacetylene group-containing dicarboxylic acid derivative of the formula:

(I')

wherein X' is a hydroxyl group or a halogen atom, and $Y_1$ and $Y_2$ are as defined with respect to the formula I, is condensation-polymerized with a diamino compound or/and a dihydroxyl compound. The condensation polymerization may be conducted by a usual method such as a low temperature solution condensation polymerization or an interfacial condensation polymerization as disclosed in e.g. "New Experimental Chemistry Lecture —Polymer Chemistry" published by Maruzen K.K. By using a plurality of monomers in such a low temperature solution condensation polymerization or an interfacial condensation polymerization, it is possible to obtain a copolymer containing diacetylene groups. Further, by using a monofunctional monomer, the molecular weight of the polymer containing diacetylene groups can be controlled.

In the case of the low temperature solution condensation polymerization, the solvent is preferably an aprotic polar solvent such as N-methylpyrrolidone, N,N'-dimethylformamide, N,N-dimethylacetamide, hexamethylphosphoramide or dimethylsulfoxide. A salt such as lithium chloride or potassium chloride may also be present in the polymerization solvent. There is no particular restriction as to the polymerization temperature. However, the polymerization is usually conducted at a temperature within a range of from −20 to 100° C. After completion of the polymerization reaction, the reaction solution is poured into a poor solvent for the polymer to precipitate the polymer, which is then collected by filtration, washed and dried under reduced pressure to obtain the desired polymer containing diacetylene groups having a high molecular weight.

In the case of the interfacial solution condensation polymerization, a diamine compound or/and a dihydroxyl compound are dissolved in an aqueous phase together with a base such as sodium hydroxide or potassium hydroxide, and a solution obtained by dissolving a diacetylene dicarboxylic acid chloride of the formula I' in a solvent such as cyclohexane or chloroform which is not soluble in water, is added under vigorous agitation for polymerization. The reaction temperature is from −20 to 100° C., and the reaction time is from a few minutes to a few hours. After completion of the reaction, the polymer obtained is separated, washed and dried under reduced pressure to obtain the desired polymer containing diacetylene groups having a high molecular weight.

The diacetylene compound to be used for the production of the polymer containing diacetylene groups according to the present invention, is a dicarboxylic acid derivative represented by the formula I'. From the view point of the reactivity of the diacetylene groups in the resulting polymer and the mechanical properties such as the strength and modulus of elasticity of the shaped product obtained by the cross linking reaction of the diacetylene groups, each of $Y_1$ and $Y_2$ is preferably a hydrogen atom, a methyl group or a chlorine atom, and it is preferably bonded to the p-or m-position on the aromatic ring. Particularly preferred is a polymer obtained by using a diacetylene compound wherein each of $Y_1$ and $Y_2$ is a hydrogen atom, and it is bonded at the p-position on the aromatic ring.

The diamino compound and the dihydroxyl compound to be used for the production of a polymer containing diacetylene groups by using the diacetylene compound of the formula I' in the present invention, are compounds represented by the following formulas:

(II)

(III)

wherein R is a hydrogen atom or a monovalent organic group having from 1 to 10 carbon atoms, and $Z_1$ and $Z_2$ may be the same or different and each represents a bivalent organic group having from 1 to 24 carbon atoms.

Each of $Z_1$ and $Z_2$ in the formulas II and III is a bivalent organic group having from 1 to 24 carbon atoms, which includes an aliphatic group such as $-CH_2-$, $-CH_2CH_2-$, $-C_3H_6-$, $-\mathit{l}\,C_4H_8-$, $-C_5H_{10}-$, $-C_6H_{12}-$, $-C_8H_{16}-$, $-C_{10}H_{20}-$ or $-CH_2-CH_3CH-$, and an aromatic group such as or

-continued

The bivalent organic group may have a part or all hydrogen atoms thereof substituted by a functional group such as a halogen atom, a nitro group, an amino group, a cyano group, a carbonyl group, a carboxyl group, an alkoxyl group or an amide group, as represented by $-CF_2-$, $-C_2F_4-$,

Further, the bivalent organic group may be the one connected by an ether linkage, an ester linkage, an amido linkage, a carbonyl group, a sulfonyl group or a thioether linkage, as represented by Further, each of $Z_1$ and $Z_2$ may be the one having a diacetylene group introduced in its structure, as represented by $-Z_3-C\equiv C-C\equiv C-Z_4$ wherein each of $Z_3$ and $Z_4$ is a bivalent organic group having from 1 to 10 carbon atoms among those described above with respect to $Z_1$ and $Z_2$.

R in the formula II is a hydrogen atom or a monovalent organic group having from 1 to 10 carbon atoms, which includes $CH_3-$, $C_2H_5-$, $C_3H_7-$, $C_4H_9-$, $C_5H_{11}-$, $C_6H_{13}-$, wherein $R_3$ is a substituent on the aromatic ring, such as a hydrogen atom, a halogen atom, an alkyl group or a nitro group.

Specific examples of the diamino compound of the formula II include p-phenylenediamine, m-phenylenediamine, tolylenediamine, xylyenediamine, o-phenylenediamine, diaminodiphenylmethane, diaminodiphenyl ether, diaminodiphenylsulfone, diaminodiphenylsulfide, diaminonaphthalene, diaminoanthracene, diaminobiphenyl, 1,4-bis(4-aminophenoxy)-benzene, 1,3-bis(4-aminophenoxy)-benzene, 4,4'-bis(4-aminophenoxy)-biphenyl, 4,4'-bis(4-aminophenoxy)-diphenylmethane, 4,4'-bis(4-aminophenoxy)-diphenylethane, 4,4'-bis(4-aminophenoxy)-diphenylpropane, 3,3'-diaminodiphenylbutadiyne, 4,4'-diaminodiphenylbutadiyne, hexamethylenediamine, pentamethylenediamine and ethylenediamine.

Specific examples of the dihydroxyl compound of the formula III include hydroquinone, resorcinol, chlorohydroquinone, phenylhydroquinone, biphenol, di(hydroxyphenyl)methane, 2,2-bis(4-hydroxyphenyl)-propane, 1,2-bis(4-hydroxyphenyl)-ethane, 4,4'-dihydroxydiphenylsulfide, 4,4'-dihydroxyphenyl ketone, 4,4'-dihydroxydiphenylsulfone, ethylene glycol, diethylene glycol, propylene glycol, tetramethylene glycol, pentamethylene glycol and hexamethylene glycol.

The diacetylene group-containing polymer produced by the process for producing a polymer containing diacetylene groups according to the present invention, may be a homopolymer or a copolymer. The terminal group of the polymer containing diacetylene groups produced by using the diacetylene compound of the present invention will be an amino group or a carboxyl group in the case where the diamino compound of the formula II is employed, and will be a hydroxyl group or a carboxyl group in the case where the dihydroxyl compound of the formula III is employed. However, the terminal group may be converted to other organic group, as the case requires. The organic group for such convertion may be, in the case where the polymer terminal group is an amino group, an aliphatic or aromatic hydrocarbon group such as and in the case where the polymer terminal group is a carboxyl group, an aliphatic or aromatic hydrocarbon group such as -continued and in the case where the polymer terminal group is a hydroxyl group, an aliphatic or aromatic hydrocarbon group such as Now, the present invention will be described in detail with reference to Examples. However, it should be understood that the present invention is by no means restricted by these specific Examples. In these Examples, "parts" means "parts by weight". Further, in the

EXAMPLE 1

In a four necked flask having a capacity of 1 liter and equipped with a stirrer, a reflux condenser, a thermometer, a dropping device and an oxygen supply tube, 5 parts of copper chloride and 5.3 parts of tetraethylethylenediamine were dissolved in 500 parts of acetone, and the mixture was stirred for 30 minutes under an oxygen stream.

Figure 1:
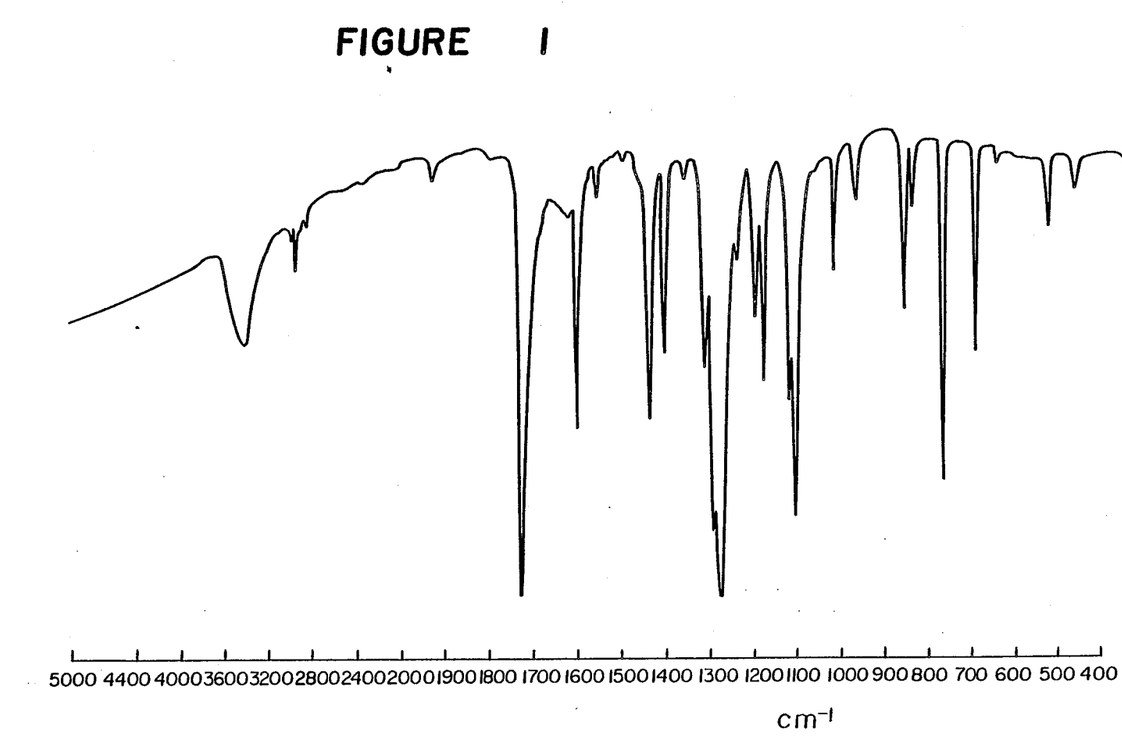
FIG. 1 is the IR spectrum of the compound obtained in Example 1.

Then, 80 parts of methyl p-ethynylbenzoate was added thereto, and the mixture was reacted at a temperature of 50° C. for 4 hours. After completion of the reaction, the reaction solution was cooled. The precipitated solid was collected by filtration, washed with methanol and dried for one day at 60° C. under reduced pressure to obtain 79 parts (yield: 95%) of the product. This product was analyzed by its IR spectrum and NMR spectrum, and it was confirmed to be the desired 1,4-bis(4-methoxycarbonylphenyl)-butadiyne. The melting point was from 188 to 189° C. The IR spectrum of this compound is shown in FIG. 1.

EXAMPLE 2

80 parts (yield: 93%) of a product was obtained in the same manner as in Example 1 except that 87 parts of ethyl p-ethynylbenzoate was used instead of 80 parts of methyl p-ethynylbenzoate of Example 1.

Figure 2:
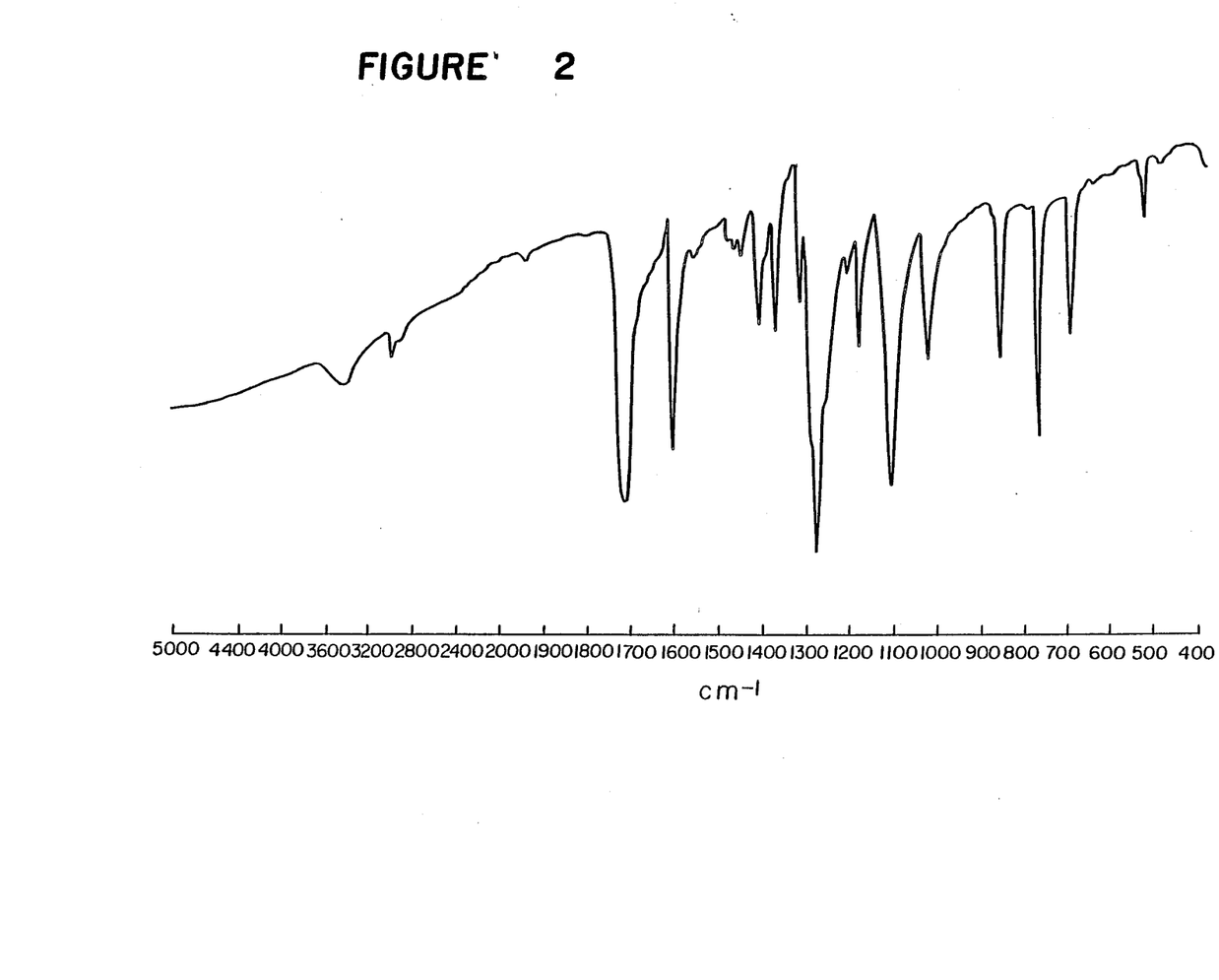
FIG. 2 is the IR spectrum of the compound obtained in Example 2.

This product was analyzed by its IR spectrum and NMR spectrum, and it was confirmed to be the desired 1,4-bis(4-ethoxycarbonylphenyl)-butadiyne. The melting point was from 158 to 159° C. The IR spectrum of this compound is shown in FIG. 2.

EXAMPLE 3

Figure 3:
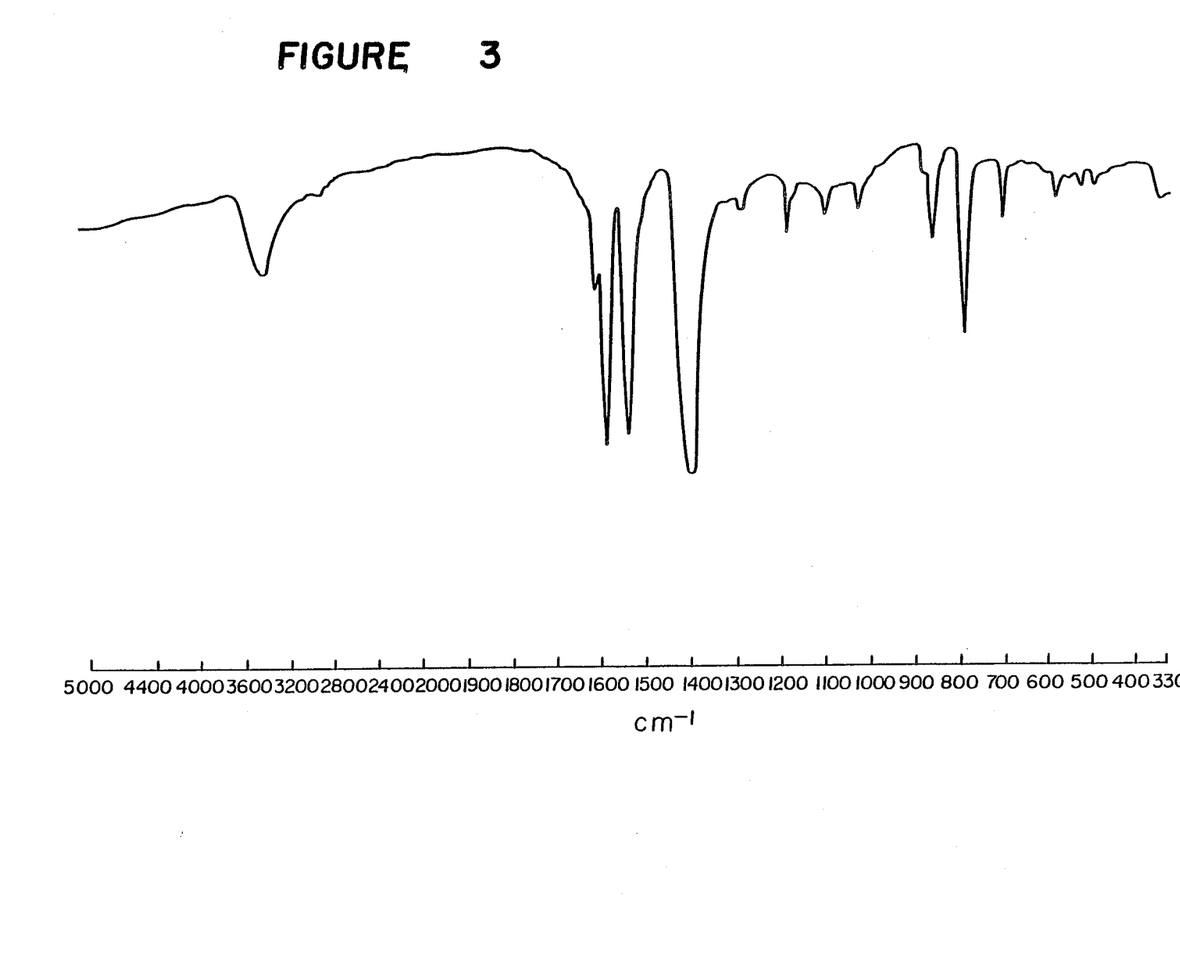
FIG. 3 is the IR spectrum of the compound obtained in Example 3.

In a four necked flask having a capacity of 1 liter and equipped with a stirrer, a reflux condenser, a thermometer, a dropping device and a nitrogen supply tube, 17.3 parts of 1,4-bis(4-ethoxycarbonylphenyl)-butadiyne obtained in Example 2 was dissolved in 100 parts of dioxane and 500 parts of ethanol, and a solution having 8 parts of sodium hydroxide dissolved in 100 parts of ethanol was dropwise added under a nitrogen stream. The mixture was reacted for 4 hours under heating and then cooled. The precipitated solid was collected by filtration, washed and then dried for one day at 60° C under reduced pressure, to obtain 17 parts (yield: 88%) of a product. This product was analyzed by its IR spectrum, and it was confirmed to be the desired 1,4-bis(4-sodiumoxycarbonylphenyl)-butadiyne. The IR spectrum of this compound is shown in FIG. 3.

EXAMPLE 4

In Example 3, after the reaction under heating for 4 hours following the addition of sodium hydroxide, the solvent was distilled off without separating the precipitated solid. Then, 500 parts of water was added and the residue was dissolved. This solution was acidified by an addition of hydrochloric acid to precipitate a solid. The solid was collected by filtration, washed and then dried for 1 day at 60° C. under reduced pressure to obtain 14 parts of a product.

Figure 4:
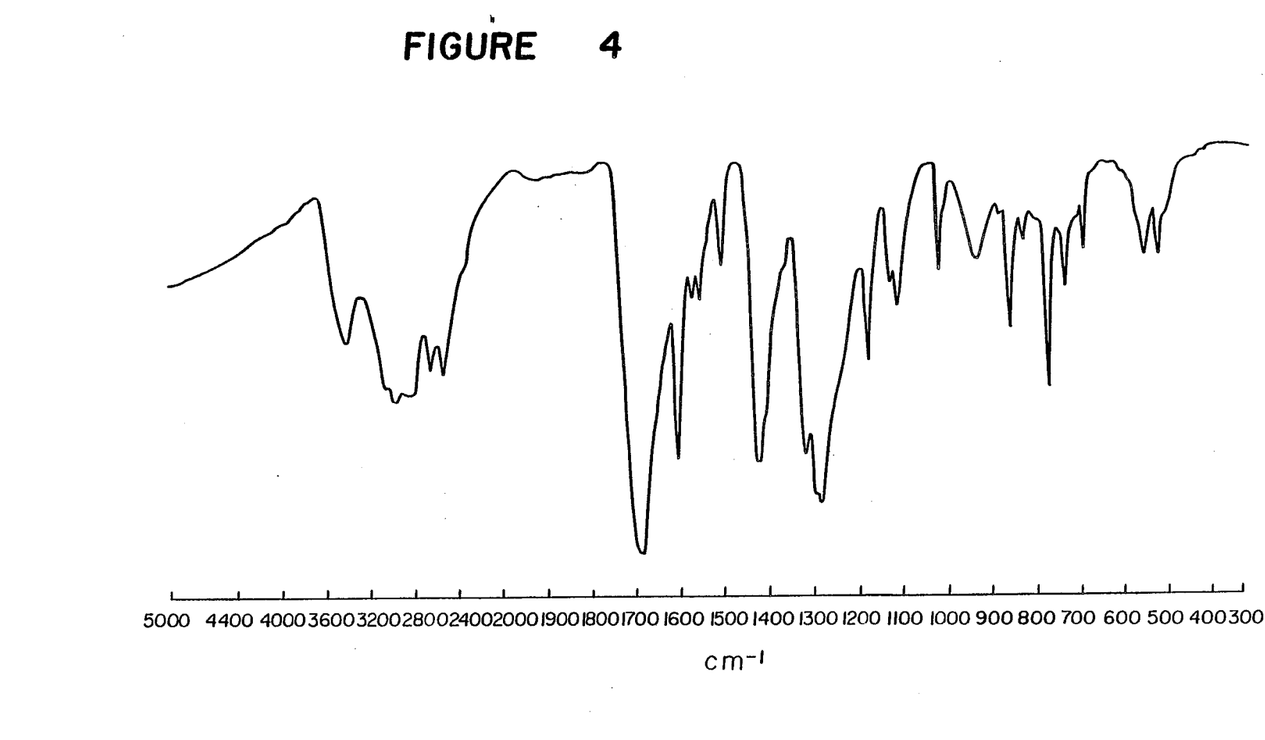
FIG. 4 is the IR spectrum of the compound obtained in Example 4.

This product was analyzed by its IR spectrum, and it was confirmed to be the desired 1,4-bis(4-hydroxycarbonylphenyl)-butadiyne. The yield was 96%. The IR spectrum of this compound is shown in FIG. 4.

EXAMPLE 5

Into a four necked flask having a capacity of 1 liter and equipped with a stirrer, a reflux condenser, a thermometer and a nitrogen supply tube, 14.5 parts of 1,4-bis(4-hydroxycarbonylphenyl)-butadiyne obtained in Example 4, 500 parts of thionyl chloride and 0.5 part of dimethylformamide were charged and reacted under reflux and heating for 8 hours. After completion of the reaction, the reaction solution was concentrated to precipitate a solid. The solid was collected by filtration, washed and then dried for 1 day at 60° C. under reduced pressure to obtain 14.8 parts of a product.

Figure 5:
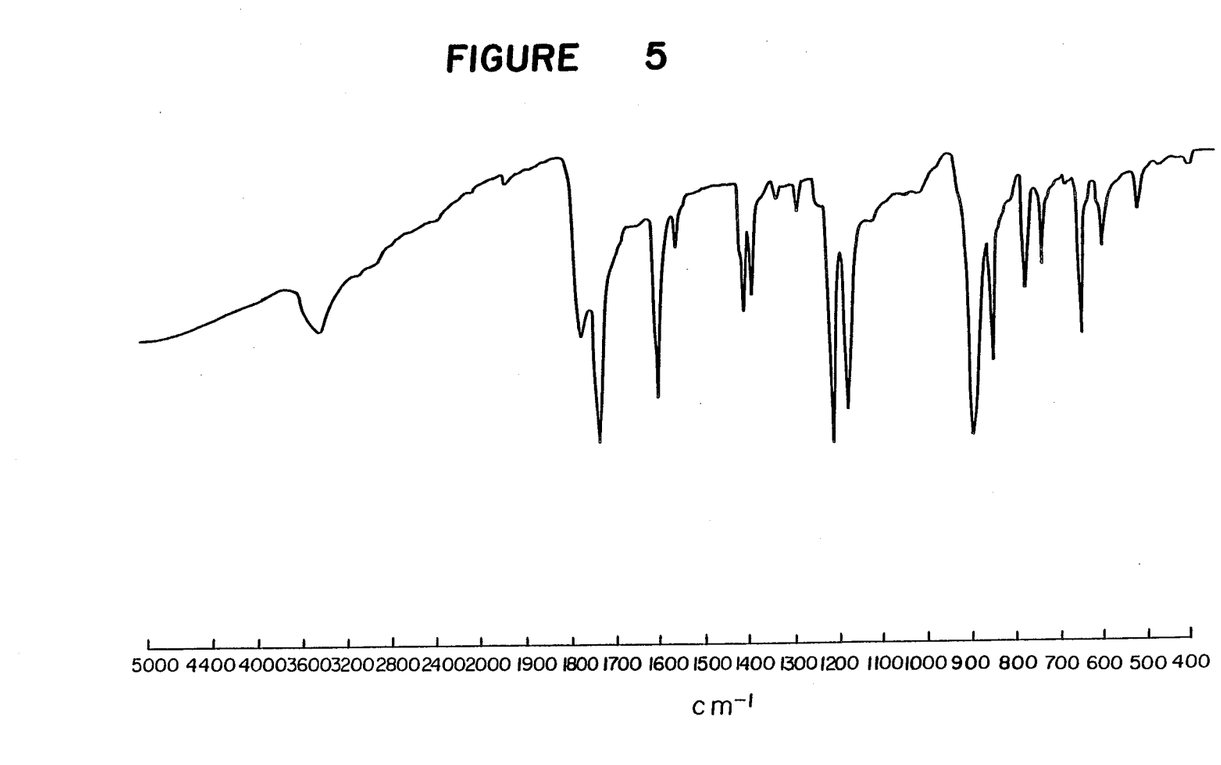
FIG. 5 is the IR spectrum of the compound obtained in Example 5.

This product was analyzed by its IR spectrum and NMR spectrum, and it was confirmed to be the desired 1,4-bis(4-chloroformylphenyl)-butadiyne. The yield was 91%. The melting point was from 175 to 177° C. The IR spectrum of this compound is shown in FIG. 5.

EXAMPLE 6

Preparation of

In a four necked flask having a capacity of 1 liter and equipped with a stirrer, a nitrogen supply tube and a thermometer, 10.8 parts (0.1 mol) of m-phenylenediamine was dissolved in 300 parts of dry N-methylpyrrolidone under a nitrogen stream, and the solution was cooled to 5° C. To this solution, 32.7 parts (0.1 mol) of 1,4-bis(4-chloroformylphenyl)-butadiyne was added, and the mixture was reacted at 5° C. for 1 hour and then at room temperature for further 3 hours. The reaction solution thereby obtained was poured into a large excess of methanol to precipitate a polymer. The polymer was washed with methanol and then dried under reduced pressure.

The yield of the polymer was substantially quantitative. From its IR spectrum, the product was confirmed to be the desired diacetylene group-containing polyamide. The viscosity of the polymer was 0.54.

EXAMPLE 7

Preparation of

A product was obtained in the same manner as in Example 6 except that p-phenylenediamine was used instead of m-phenylenediamine of Example 6, and 5% by weight of lithium chloride was added to the dry n-methylpyrrolidone as the solvent.

From its IR spectrum, the product was confirmed to be the desired diacetylene group-containing polyamide. The viscosity of the polymer was 0.48.

EXAMPLE 8

Preparation of

A product was obtained in the same manner as in Example 6 except that oxydianiline was used instead of m-phenylenediamine of Example 6.

From its IR spectrum, the product was confirmed to be the desired diacetylene group-containing polyamide. The viscosity of the polymer was 1.27.

EXAMPLE 9

Preparation of

A product was obtained in the same manner as in Example 6 except that hexamethylenediamine was used instead of m-phenylenediamine of Example 6.

From its IR spectrum, the product was confirmed to be the desired diacetylene group-containing polyamide. The viscosity of the polymer was 0.27.

EXAMPLE 10

Preparation of

In a four necked flask having a capacity of 1 liter and equipped with a stirrer, a nitrogen supply tube and a thermometer, 23.2 parts (0.1 mol) of 3,3'-diaminodiphenylbutadiyne was dissolved in 300 parts of dry N-methylpyrrolidone under a nitrogen stream, and the solution was cooled to 5° C. To this solution, 32.7 parts (0.1 mol) of 1,4-bis(4-chloroformylphenyl)-butadiyne was added, and the mixture was reacted at 5° C. for 1 hour and then at room temperature for further 3 hours. The reaction solution thereby obtained was poured into a large excess of methanol to precipitate a polymer. The polymer was washed with methanol and then dried under reduced pressure.

The yield of the polymer was substantially quantitative. From its IR spectrum, the product was confirmed to be the desired diacetylene group-containing polyamide. The viscosity of the polymer was 0.32.

EXAMPLE 11

Preparation of

A product was obtained in the same manner as in Example 10 except that 4,4'-diaminodiphenylbutadiyne was used instead of m-phenylenediamine of Example 10, and 5% by weight of lithium chloride was added to the dry N-methylpyrrolidone as the solvent.

From its IR spectrum, the product was confirmed to be the desired diacetylene group-containing polyamide. The viscosity of the polymer was 0.29.

EXAMPLE 12

Preparation of

A product was obtained in the same manner as in Example 10 except that 2,4-hexadiyne-1,6-diamine was used instead of m-phenylenediamine of Example 10.

From its IR spectrum, the product was confirmed to be the desired diacetylene group-containing polyamide. The viscosity of the polymer was 0.36.

EXAMPLE 13

Preparation of

In a four necked flask having a capacity of 1 liter and equipped with a stirrer, a nitrogen supply tube and a thermometer, 32.7 parts (0.1 mol) of 1,4-bis(4-chloroformylphenyl)-butadiyne was dissolved in 300 parts of N,N-dimethylacetamide (DMAc) under a nitrogen stream, and the solution was cooled to 5° C. or lower. To this solution, 22.8 parts (0.1 mol) of 2,2-bis(4-hydroxyphenyl)-propane (bisphenol A) was added. The mixture was reacted at 5° for 1 hour and then at room temperature for further 3 hours. The reaction solution thereby obtained was poured into methanol to precipitate a polymer. The polymer was isolated, washed with methanol and then dried under reduced pressure.

The yield of the polymer was quantitative. From its IR spectrum, the product was confirmed to be the desired diacetylene group-containing polyester.

EXAMPLE 14

Preparation of

A product was obtained in the same manner as in Example 13 except that 4,4'-biphenol was used instead of bisphenol A of Example 13.

From its IR spectrum, the product was confirmed to be the desired polyester.

EXAMPLE 15

Preparation of

In a four necked flask having a capacity of 1 liter and equipped with a stirrer, a nitrogen supply tube and a thermometer, 32.7 parts (0.1 mol) of 1,4-bis(4 chloroformylphenyl)-butadiyne was dissolved in 300 parts of N,N-dimethylacetamide (DMAc) under a nitrogen stream, and the solution was cooled to 5° C. or lower. To this solution, 11.0 parts (0.1 mol) of 2,4-hexadiyne-1,6-diol was added. The mixture was reacted at 5° C. for 1 hour and then at room temperature for further 3 hours. The reaction solution thereby obtained was poured into methanol to precipitate a polymer. The polymer was isolated, washed with methanol and then dried under reduced pressure.

The yield of the polymer was quantitative. Further from its IR spectrum, the product was confirmed to be the desired diacetylene-containing polyester.

EXAMPLE 16

Preparation of

A product was obtained in the same manner as in Example 15 except that 1,4-bis(4-hydroxyphenyl)-butadiyne was used instead of 2,4-hexadiyne-1,6-diol of Example 15.

From its IR spectrum, the product was confirmed to be the desired polyester.

APPLICATION EXAMPLE 1

The diacetylene group-containing polyamide obtained in Example 6 was filled in a molding cylinder, then placed on a hydraulic press having heating plates capable of being deaerated under reduced pressure and subjected to heat press molding under pressure of 10,000 atm at a temperature of 300° C. for 2 hours. The molded product thereby obtained was a black disk having a diameter of 3.5 cm.

From the molded product thus obtained, a test piece having a height of 2 mm, a width of 5 mm and a length of 3.3 cm was cut out. By using the test piece, the flexural modulus of elasticity was measured by a dynamic viscoelasticity automatic measuring device (Vibron DDV-III, manufactured by Kabushiki Kaisha Orientec), whereby the modulus of elasticity of the molded product was found to be 7.2 GPa.

APPLICATION EXAMPLES 2 to 4

A molded product was prepared in the same manner as in Application Example 1 except that the molding conditions were changed. The results are shown in Table 1.

APPLICATION EXAMPLES 5 to 8

A molded product was prepared in the same manner as in Application Examples 1 to 4 except that the polymer obtained in Example 7 was employed. The results are shown in Table 1.

TABLE 1

| Application Example No. | Molding conditions | | | Mechanical Property Flexural modulus of elasticity (GPa) |
|---|---|---|---|---|
| | Pressure (atm) | Temp. (°C.) | Pressing time (hr) | |
| 1 | 10,000 | 300 | 2 | 7.2 |
| 2 | 10,000 | 300 | 4 | 7.6 |
| 3 | 10,000 | 320 | 2 | 7.5 |
| 4 | 15,000 | 300 | 2 | 7.8 |
| 5 | 10,000 | 300 | 2 | 6.9 |
| 6 | 10,000 | 300 | 4 | 7.2 |
| 7 | 10,000 | 320 | 2 | 7.4 |
| 8 | 15,000 | 320 | 2 | 7.9 |

APPLICATION EXAMPLE 9

The diacetylene group-containing polyamide obtained in Example 10 was filled in a molding cylinder, then placed on a hydraulic press having heating plates capable of being deaerated under reduced pressure and subjected to heat press molding under a pressure of 10,000 atm at a temperature of 300° C. for 2 hours. The molded product thereby obtained was a black disk having a diameter of 3.5 cm.

From the molded product thus obtained, a test piece having a height of 2 mm, a width of 5 mm and a length of 3.3 cm was cut out. By using the test piece, the flexural modulus of elasticity was measured by a dynamic viscoelasticity automatic measuring device (Vibron DDV-III, manufactured by Kabushiki Kaisha Orientec), whereby the modulus of elasticity of the molded product was found to be 7.8 GPa.

APPLICATION EXAMPLES 10 TO 12

A shaped product was prepared in the same manner as in Application Example 9 except that the molding conditions were changed. The results are shown in Table 2.

APPLICATION EXAMPLES 13 TO 16

A molded product was prepared in the same manner as in Application Examples 1 to 4 except that the polymer obtained in Example 11 was used. The results are shown in Table 2.

APPLICATION EXAMPLES 17 AND 18

A molded product was prepared in the same manner as in Application Examples 1 to 4 except that the polymer obtained in an Example 12 was used. The results are shown in Table 2.

TABLE 2

| Application Example No. | Molding conditions | | | Mechanical Property Flexural modulus of elasticity (GPa) |
|---|---|---|---|---|
| | Pressure (atm) | Temp. (°C.) | Pressing time (hr) | |
| 9 | 10,000 | 300 | 2 | 7.6 |
| 10 | 10,000 | 300 | 4 | 7.8 |
| 11 | 15,000 | 280 | 2 | 7.6 |
| 12 | 15,000 | 300 | 2 | 8.0 |
| 13 | 10,000 | 300 | 2 | 7.3 |
| 14 | 10,000 | 300 | 4 | 7.4 |
| 15 | 10,000 | 320 | 2 | 7.6 |
| 16 | 15,000 | 300 | 2 | 7.6 |
| 17 | 10,000 | 100 | 2 | 6.8 |
| 18 | 15,000 | 100 | 2 | 7.9 |

APPLICATION EXAMPLE 19

The diacetylene group-containing polyester obtained in Example 13 was filled in a molding cylinder, then placed on a hydraulic press having heating plates capable of being dearated under reduced pressure and subjected to heat press molding under a pressure of 10,000 atm at a temperature of 300° C. for 2 hours. The molded product thereby obtained was a black disk having a diameter of 3.5 cm.

From the molded product thus obtained, a test piece having a height of 2 mm, a width of 5 mm and a length of 3.3 cm was cut out.

By using the test piece, the flexural modulus of elasticity was measured by a dynamic viscoelasticity automatic measuring device (Vibron DDV-III, manufactured by Kabushiki Kaisha Orientec), whereby the modulus of elasticity of the molded product was found to be 6.4 GPa.

APPLICATION EXAMPLES 20 TO 22

A molded product was prepared in the same manner as in Application Example 19 except that the molding conditions were changed. The results are shown in Table 3.

APPLICATION EXAMPLES 23 TO 26

A molded product was prepared in the same manner as in Application Example 19 except that the polymer obtained in Example 14 was used and the molding conditions were as shown in Table 3. The results are shown in Table 3.

TABLE 3

| Application Example No. | Molding conditions ||| Mechanical Property Flexural modulus of elasticity (GPa) |
|---|---|---|---|---|
| | Pressure (atm) | Temp. (°C.) | Pressing time (hr) | |
| 19 | 10,000 | 300 | 2 | 6.4 |
| 20 | 10,000 | 300 | 4 | 6.7 |
| 21 | 10,000 | 320 | 2 | 6.8 |
| 22 | 15,000 | 300 | 2 | 7.0 |
| 23 | 10,000 | 300 | 2 | 6.8 |
| 24 | 10,000 | 300 | 4 | 7.1 |
| 25 | 15,000 | 300 | 2 | 7.5 |
| 26 | 15,000 | 330 | 2 | 7.8 |

APPLICATION EXAMPLE 27

The diacetylene group-containing polyester obtained in Example 15 was filled in a molding cylinder, then placed on a hydraulic press having heating plates capable of being deaerated under reduced pressure and subjected to heat press molding under a pressure of 10,000 atm at a temperature of 300° C. for 2 hours. The molded product thereby obtained was a black disk having a diameter of 3.5 cm. From the molded product thus obtained, a test piece having a height of 2 mm, a width of 5 mm and a length of 3.3 cm was cut out. By using the test piece, the flexural modulus of elasticity was measured by a dynamic viscoelasticity automatic measuring device (Vibron DDV-III, manufactured by Kabushiki Kaisha Orientec), whereby the modulus of elasticity of the molded product was found to be 7.5 GPa.

APPLICATION EXAMPLES 28 TO 30

A molded product was prepared in the same manner as in Application Example 27 except that the molding conditions were changed. The results are shown in Table 4.

APPLICATION EXAMPLES 31 TO 34

A molded product was prepared in the same manner as in Application Example 27 except that the polymer obtained in Example 16 was used and the molding conditions were as shown in Table 4. The results are shown in Table 4.

TABLE 4

| Application Example No. | Molding conditions ||| Mechanical Property Flexural modulus of elasticity (GPa) |
|---|---|---|---|---|
| | Pressure (atm) | Temp. (°C.) | time (hr) | |
| 27 | 10,000 | 100 | 2 | 7.5 |
| 28 | 10,000 | 100 | 4 | 7.6 |
| 29 | 15,000 | 100 | 2 | 7.9 |
| 30 | 15,000 | 130 | 4 | 8.4 |
| 31 | 10,000 | 200 | 2 | 7.3 |
| 32 | 10,000 | 200 | 2 | 7.4 |
| 33 | 15,000 | 200 | 2 | 7.5 |
| 34 | 15,000 | 250 | 2 | 8.2 |

What is claimed is:

1. A diacetylene compound of the formula:

or wherein X is hydroxyl, halogen, alkoxy, a monavalent hydrocarbon having from 1 to 20 carbon atoms or a —OM group wherein M is an alkali metal, and each of $Y_1$ and $Y_2$, which are the same or different, is hydrogen, a monavalent organic group having from 1 to 20 carbon atoms or halogen.

2. The diacetylene compound according to claim 1, wherein X is a hydroxyl group, a halogen atom, an alkoxy group having from 1 to 6 carbon atoms, a —ONa group or a —OK group.

3. The diacetylene compound according to claim 1, wherein X is a hydroxyl group or a halogen atom.

4. The diacetylene compound according to claim 3, wherein the halogen atom is Cl or Br.

5. The diacetylene compound according to claim 1, wherein each of $Y_1$ and $Y_2$ is a hydrogen atom.

6. The diacetylene compound according to claim 1, which has the formula:

wherein X, $Y_1$ and $Y_2$ are as defined with respect to the formula I.

7. The diacetylene compound according to claim 1, which is a coupling reaction product of an ehtynyl compound of the formula:

wherein X is as defined with respect to the formula I and Y is the same as $Y_1$ or $Y_2$ as defined with respect to the formula I.

8. The diacetylene compound according to claim 1, wherein said diacetylene compound is a member selected from the group consisting of 1,4-bis(4-methoxycarbonylphenyl)-butadiyne, 1,4-bis(4-ethoxycarbonylphenyl)-butadiyne, 1,4-bis(4-butoxycarbonylphenyl)-butadiyne, 1,4-bis(4-phenoxycarbonylphenyl)-butadiyne, 1,4-bis(4-benzyloxyphenyl)-butadiyne, 1,4-bis(3-methoxycarbonylphenyl)-butadiyne, 1,4-bis(3-ethyoxylcarbonylphenyl)-butadiyne, 1,4-bis(3-phenoxycarbonylphenyl)-butadiyne, 1,4-bis(3-methyl-4-methoxycarbonylphenyl)-butadiyne, 1,4-bis(3-methyl-4-ethoxycarbonylphenyl)-butadiyne, 1,4-bis(3-chloro-4-methoxycarbonylphenyl)-butadiyne, 1,4-bis(3-chloro-4-ethoxycarbonylphenyl)-butadiyne, 1,4-bis(4-methlycarbonylphenyl)-butadiyne, 1,4-bis(4-ethylcarbonylphenyl)-butadiyne, 1,4-bis(4-phenylcarbonylphenyl)-butadiyne, 1,4-bis(3-methylcarbonylphenyl)-butadiyne, 1,4-bis(3-ethylcarbonylphenyl)-butadiyne, 1,4-bis(3-methyl-4-methylcarbonylphenyl)-butadiyne, 1,4-bis(2-methyl-4-methylcarbonylphenyl)-butadiyne, 1,4-bis(3-methyl-5-methylcarbonylphenyl)-butadiyne, 1,4-bis(3-chloro-4-ethylcarbonylphenyl)-butadiyne, 1,4-bis(3-chloro-5-ethylcarbonylphenyl)-butadiyne, 1,4-bis(4-hydroxycarbonylphenyl)-butadiyne, 1,4-bis(3-hydroxycarbonylphenyl)-butadiyne, 1,4-bis(3-methyl-4-hydroxycarbonylphenyl)-butadiyne, 1,4-bis(3-ethyl-4-hydroxycarbonylphenyl)-butadiyne, 1,4-bis(3-methyl-5-hydroxycarbonylphenyl)-butadiyne, 1,4-bis(2-ethyl-5-hydroxycarbonylphenyl)-butadiyne, 1,4-bis(3-chloro-4-hydroxycarbonylphenyl)-butadiyne, 1,4-bis(3-chloro-5-hydroxycarbonylphenyl)-butadiyne, 1,4-bis(2-chloro-4-hydroxycarbonylphenyl)-butadiyne, 1,4-bis(2-chloro-3-hydroxycarbonylphenyl)-butadiyne, 1,4-bis(4 sodiumoxycarbonylphenyl)-butadiyne, 1,4-bis(3-sodiumoxycarbonylphenyl)-butadiyne, 1,4-bis(4-potassiumoxycarbonylphenyl)-butadiyne, 1,4-bis(4-chloroformylphenyl)-butadiyne, 1,4-bis(3-chloroformylphenyl)-butadiyne, 1,4-bis(3-methyl-4-chloroformylphenyl)-butadiyne, 1,4-bis(2-methyl-4-chloroformylphenyl)-butadiyne, 1,4-bis(3-chloro-4-chloroformylphenyl)-butadiyne, 1,4-bis(3-chloro-5-chloroformylphenyl)-butadiyne, 1,4-bis(4-bromoformylphenyl)-butadiyne, and 1,4-bis(3-bromoformylphenyl)-butadiyne.

9. A diacetylene compound of the formula:

or wherein X is hydroxyl, halogen, or alkoxy and each of $Y_1$ and $Y_2$, which are the same or different, is hydrogen, a monovalent organic group having from 1 to 20 carbon atoms or halogen.

* * * * *